(12) United States Patent
Laitinen et al.

(10) Patent No.: US 10,189,789 B2
(45) Date of Patent: Jan. 29, 2019

(54) PROCESS FOR THE PREPARATION OF ANDROGEN RECEPTOR ANTAGONISTS AND INTERMEDIATES THEREOF

(71) Applicant: Orion Corporation, Espoo (FI)

(72) Inventors: Ilpo Laitinen, Espoo (FI); Oskari Karjalainen, Helsinki (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 15/564,878

(22) PCT Filed: Apr. 8, 2016

(86) PCT No.: PCT/FI2016/050220
§ 371 (c)(1),
(2) Date: Oct. 6, 2017

(87) PCT Pub. No.: WO2016/162604
PCT Pub. Date: Oct. 13, 2016

(65) Prior Publication Data
US 2018/0099938 A1    Apr. 12, 2018

(30) Foreign Application Priority Data
Apr. 9, 2015   (FI) ..................... 20150111

(51) Int. Cl.
| | | |
|---|---|---|
| C07D 231/12 | (2006.01) | |
| C07D 405/04 | (2006.01) | |
| C07D 403/12 | (2006.01) | |
| C07D 207/34 | (2006.01) | |
| C07D 207/337 | (2006.01) | |

(52) U.S. Cl.
CPC ....... *C07D 231/12* (2013.01); *C07D 207/337* (2013.01); *C07D 207/34* (2013.01); *C07D 403/12* (2013.01); *C07D 405/04* (2013.01)

(58) Field of Classification Search
None
See application file for complete search history.

(56) References Cited

U.S. PATENT DOCUMENTS 8,921,378 B2*   12/2014   Tormakangas ....... C07D 401/04
                                                                          514/259.1

FOREIGN PATENT DOCUMENTS

WO    WO 2012/143599 A1    10/2012

\* cited by examiner

*Primary Examiner* — Kamal A Saeed
(74) *Attorney, Agent, or Firm* — Finnegan, Henderson, Farabow, Garrett & Dunner, L.L.P.

(57) ABSTRACT

The present invention relates to an improved process for the preparation of carboxamide structured androgen receptor (AR) antagonists such as N—((S)-1-(3-(3-chloro-4-cyanophenyl)-1H-pyrazol-1-yl)-propan-2-yl)-5-(1-hydroxyethyl)-1H-pyrazole-3-carboxamide (1A) and key intermediates thereof such as 2-chloro-4-(1H-pyrazol-3-yl)benzonitrile (V). AR antagonists are useful in the treatment of cancer, particularly prostate cancer and other diseases where AR antagonism is desired.

(1A)

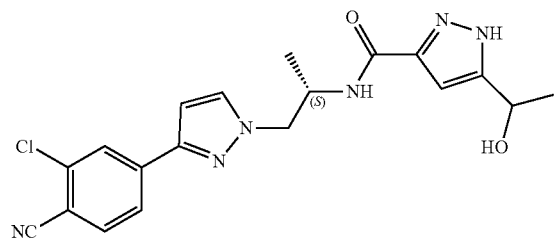

29 Claims, No Drawings

PROCESS FOR THE PREPARATION OF ANDROGEN RECEPTOR ANTAGONISTS AND INTERMEDIATES THEREOF

This is a national stage application under 35 U.S.C. § 371 of International Patent Application No. PCT/FI2016/050220, filed Apr. 8, 2016, which claims the benefit of Finnish Patent Application No. 20150111, filed Apr. 9, 2015, both of which are incorporated herein by reference.

TECHNICAL FIELD

The present invention relates to an improved process for the preparation of carboxamide structured androgen receptor antagonists such as N—((S)-1-(3-(3-chloro-4-cyanophenyl)-1H-pyrazol-1-yl)-propan-2-yl)-5-(1-hydroxyethyl)-1H-pyrazole-3-carboxamide (1A) and key intermediates thereof such as 2-chloro-4-(1H-pyrazol-3-yl)benzonitrile (V).

BACKGROUND OF THE INVENTION

The compound N—((S)-1-(3-(3-chloro-4-cyanophenyl)-1H-pyrazol-1-yl)-propan-2-yl)-5-(1-hydroxyethyl)-1H-pyrazole-3-carboxamide of formula (1A) and derivatives thereof have been disclosed in WO 2011/051540. Compound of formula (1A) and its derivatives are potent androgen receptor (AR) antagonists that are useful in the treatment of cancer, particularly prostate cancer and other diseases where AR antagonism is desired.

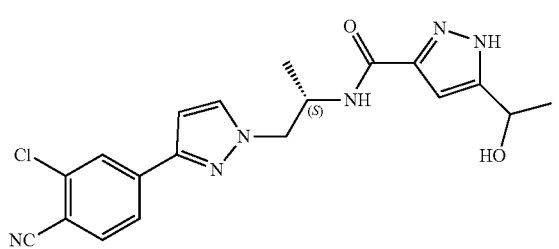

(1A)

WO 2011/051540 discloses a process for the preparation of the compound of formula (1A) through 2-chloro-4-(1H-pyrazol-3-yl)benzonitrile intermediate of formula (V). The intermediate of formula (V) was prepared as shown in Scheme I:

SCHEME 1

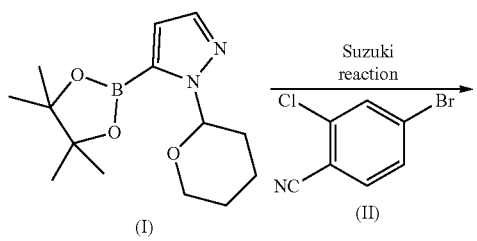

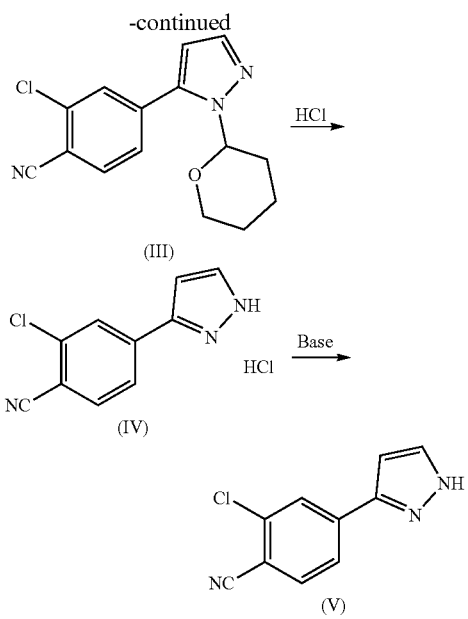

This process comprises reacting 1-(tetrahydro-2H-pyran-2-yl)-1H-pyrazole-5-boronic acid pinacol ester (I) with 4-bromo-2-chlorobenzonitrile (II) in a Suzuki reaction to obtain 2-chloro-4-(1-(tetrahydro-2H-pyran-2-yl)-1H-pyrazol-5-yl)-benzonitrile of formula (III). The Suzuki reaction is carried out in the presence of bis(triphenylphosphine) palladium(II) chloride catalyst and sodium carbonate base in THF-water solvent. After the reaction has completed the solvents are distilled to almost dryness and water is added to precipitate the compound of formula (III). The isolated compound of formula (III) is subsequently treated with 10% HCl in ethanol to obtain 2-chloro-4-(1H-pyrazol-3-yl)benzonitrile hydrochloride salt of formula (IV) which is isolated. Finally, 2-chloro-4-(1H-pyrazol-3-yl)benzonitrile of formula (V) is obtained by treating the compound for formula (IV) with sodium hydroxide in water-methanol solvent.

A similar process for preparing the compound of formula (V) is disclosed in WO 2012/143599. The Suzuki reaction is carried out in THF-toluene-water solvent and also a phase transfer catalyst (TBAB) is used. The isolation of the compound of formula (III) is carried out by adding water and distilling the isolated organic phase close to dryness followed by adding ethanol and filtering the crystalline product. The isolated compound of formula (III) is treated with 10% HCl in ethanol to obtain the compound of formula (IV). This compound is dissolved in methanol for treatment with activated carbon and celite. Part of methanol is distilled off and water and 50% NaOH is added. After the reaction is complete methanol is distilled off and water is added for precipitation of the compound of formula (V). The total yield of all three stages is 84.5%.

The above mentioned processes have several drawbacks. The amount of the expensive bis(triphenylphosphine)palladium(II) chloride catalyst needed to carry out the Suzuki reaction effectively is high, around 5 mol-%. The use of ethanolic HCl is impractical and the work-up of the process is very complex due to many distillations to dryness which is a difficult operation to handle in a large scale. Moreover, several isolations make the process cumbersome and lower the yield.

Thus, there is a need for a more practical and economical process that is suitable for the manufacture of intermediates such as the compound of formula (V) in a large scale.

SUMMARY OF THE INVENTION

It has now been found that the compound of formula (V) can be prepared using a process which is more practical and economical and suitable for use in a large scale. In particular, the amount of expensive palladium catalyst can be substantially reduced and the cumbersome distillation steps as well as the use of ethanolic HCl are avoided. Moreover, the number of isolation steps are reduced leading to higher yield. The levels of palladium residues found in the end product are also substantially reduced.

Thus the present invention provides a process for the preparation of 2-chloro-4-(1H-pyrazol-3-yl)benzonitrile of formula (V)

(V)

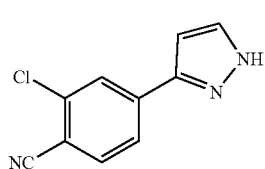

comprising the steps of a) reacting 1-(tetrahydro-2H-pyran-2-yl)-5-(4,4,5,5-tetramethyl-1,3,2-dioxaborolan-2-yl)-1H-pyrazole of formula (I)

(I)

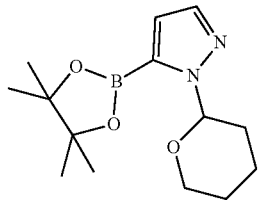

with 4-bromo-2-chlorobenzonitrile of formula (II)

(II)

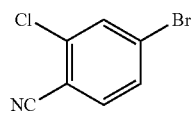

at an elevated temperature in the presence of Pd(OAc)$_2$, triphenylphosphine and a base in an acetonitrile-water solvent to form 2-chloro-4-(1-(tetrahydro-2H-pyran-2-yl)-1H-pyrazol-5-yl)benzonitrile of formula (III)

(III)

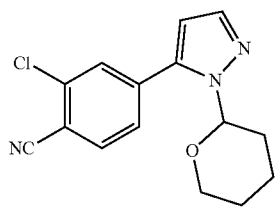

b) treating the compound of formula (III) with a catalytic amount of HCl in a methanol solvent;
c) adding a base to neutralize the mixture; and
d) isolating the compound of formula (V).

In another aspect, the present invention provides a process for the preparation of 2-chloro-4-(1H-pyrazol-3-yl)benzonitrile of formula (V)

(V)

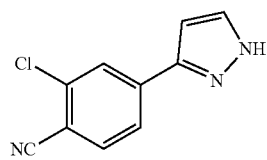

comprising the steps of a) reacting 1-(tetrahydro-2H-pyran-2-yl)-5-(4,4,5,5-tetramethyl-1,3,2-dioxaborolan-2-yl)-1H-pyrazole of formula (I)

(I)

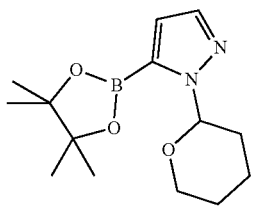

with 4-bromo-2-chlorobenzonitrile of formula (II)

(II)

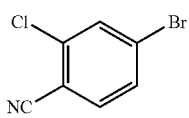

at an elevated temperature in the presence of Pd(OAc)$_2$, triphenylphosphine and a base in an acetonitrile-water solvent;
b) isolating the acetonitrile phase;
c) adding water to the cooled acetonitrile phase;
d) isolating the precipitated 2-chloro-4-(1-(tetrahydro-2H-pyran-2-yl)-1H-pyrazol-5-yl)benzonitrile of formula (III)

(III)

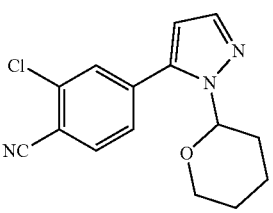

e) treating the compound of formula (III) with a catalytic amount of HCl in a methanol solvent;
f) adding a base to neutralize the mixture;
g) adding water to the mixture; and
h) isolating the precipitated compound of formula (V).

In still another aspect, the present invention provides a process for the preparation of 2-chloro-4-(1H-pyrazol-3-yl)benzonitrile of formula (V)

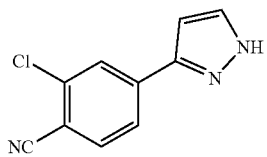
(V)

comprising the steps of
a) treating 2-chloro-4-(1-(tetrahydro-2H-pyran-2-yl)-1H-pyrazol-5-yl)-benzonitrile of formula (III)

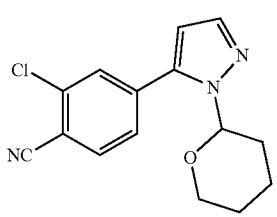
(III)

with a catalytic amount of HCl in a methanol solvent;
b) adding a base to neutralize the mixture;
c) isolating the precipitated compound of formula (V).

In still another aspect, the present invention provides a process for the preparation of 2-chloro-4-(1H-pyrazol-3-yl) benzonitrile of formula (V)

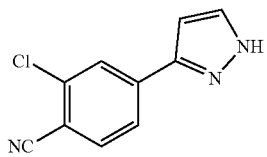
(V)

comprising the steps of
a) treating 2-chloro-4-(1-(tetrahydro-2H-pyran-2-yl)-1H-pyrazol-5-yl)-benzonitrile of formula (III)

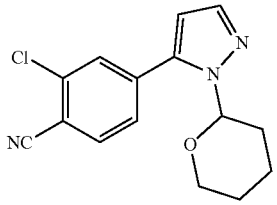
(III)

with a catalytic amount of HCl in a methanol solvent;
b) adding a base to neutralize the mixture;
c) adding water to the mixture; and
d) isolating the precipitated compound of formula (V).

In still another aspect, the present invention provides the use of the compound of formula (V) in the preparation of the compound of formula (1A), wherein the compound of formula (V) is prepared according to any of the methods disclosed above.

In still another aspect, the present invention provides a process for the preparation of 2-chloro-4-(1-(tetrahydro-2H-pyran-2-yl)-1H-pyrazol-5-yl)benzonitrile of formula (III)

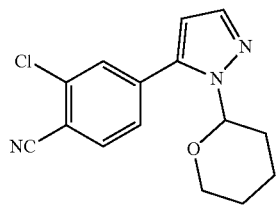
(III)

comprising the steps of
a) reacting 1-(tetrahydro-2H-pyran-2-yl)-5-(4,4,5,5-tetramethyl-1,3,2-dioxaborolan-2-yl)-1H-pyrazole of formula (I)

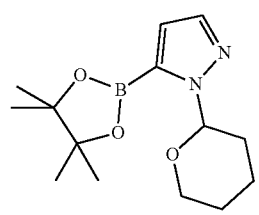
(I)

with 4-bromo-2-chlorobenzonitrile of formula (II)

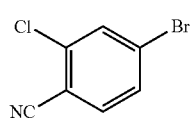
(II)

at an elevated temperature in the presence of Pd(OAc)$_2$, triphenylphosphine and a base in an acetonitrile-water solvent.

In still another aspect, the present invention provides a process for the preparation of 2-chloro-4-(1-(tetrahydro-2H-pyran-2-yl)-1H-pyrazol-5-yl)benzonitrile of formula (III)

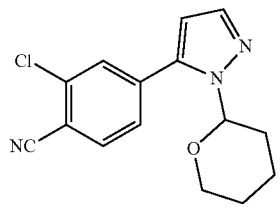
(III)

comprising the steps of
a) reacting 1-(tetrahydro-2H-pyran-2-yl)-5-(4,4,5,5-tetramethyl-1,3,2-dioxaborolan-2-yl)-1H-pyrazole of formula (I)

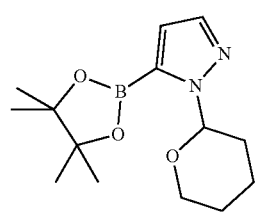
(I)

with 4-bromo-2-chlorobenzonitrile of formula (II)

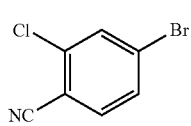
(II)

at an elevated temperature in the presence of Pd(OAc)$_2$, triphenylphosphine and a base in a acetonitrile-water solvent;
  b) isolating the acetonitrile phase;
  c) adding water to the cooled acetonitrile phase;
  d) isolating the precipitated compound of formula (III).

In still another aspect, the present invention provides the use of the compound of formula (III) in the preparation of the compound of formula (1A), wherein the compound of formula (III) is prepared according to any of the methods disclosed above.

DETAILED DESCRIPTION OF THE INVENTION

The term "mol-% of Pd(OAc)$_2$", as used herein, refers to the percentage of the amount of Pd(OAc)$_2$ catalyst (in moles) used in the reaction step in relation to the amount of starting compound (in moles). For example, if 0.005 mol of Pd(OAc)$_2$ is used per 1 mol of bromo-2-chlorobenzonitrile in the reaction step a), the mol-% of Pd(OAc)$_2$ used in step a) is (0.005/1)*100 mol-%=0.5 mol-%.

Tautomerism: As the hydrogen atom of the pyrazole ring may exist in tautomeric equilibrium between the 1- and 2-position, it is recognized by the skilled person that the formulas and chemical names disclosed herein comprising a hydrogen atom in the pyrazole ring are inclusive of the tautomer of the compound in question.

For example, the chemical name as "2-chloro-4-(1H-pyrazol-3-yl)benzonitrile" and the corresponding formula (V) is inclusive of the tautomer of the compound, namely "2-chloro-4-(1H-pyrazol-5-yl)benzonitrile".

In accordance with the present invention 2-chloro-4-(1H-pyrazol-3-yl)benzonitrile of formula (V)

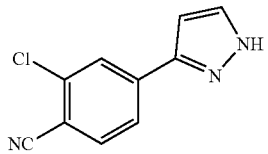
(V)

is prepared by
  a) reacting 1-(tetrahydro-2H-pyran-2-yl)-5-(4,4,5,5-tetramethyl-1,3,2-dioxaborolan-2-yl)-1H-pyrazole of formula (I)

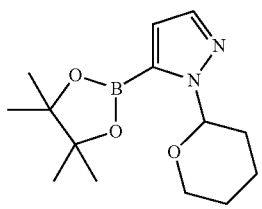
(I)

with 4-bromo-2-chlorobenzonitrile of formula (II)

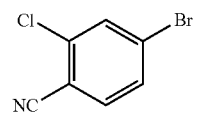
(II)

at an elevated temperature in the presence of Pd(OAc)$_2$, triphenylphosphine and a base in an acetonitrile-water solvent to form 2-chloro-4-(1-(tetrahydro-2H-pyran-2-yl)-1H-pyrazol-5-yl)benzonitrile of formula (III)

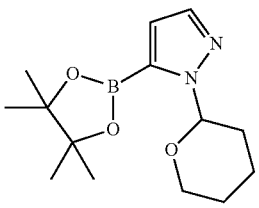
(III)

b) treating the compound of formula (III) with a catalytic amount of HCl in a methanol solvent;
  c) adding a base to neutralize the mixture; and
  d) isolating the compound of formula (V).

In accordance with the present invention, in particular, 2-chloro-4-(1H-pyrazol-3-yl)benzonitrile of formula (V)

(V)

is prepared by
  a) reacting 1-(tetrahydro-2H-pyran-2-yl)-5-(4,4,5,5-tetramethyl-1,3,2-dioxaborolan-2-yl)-1H-pyrazole of formula (I)

(I)

with 4-bromo-2-chlorobenzonitrile of formula (II)

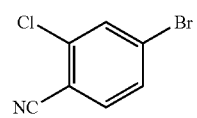
(II)

at an elevated temperature in the presence of Pd(OAc)$_2$, triphenylphosphine and a base in a acetonitrile-water solvent;
  b) isolating the acetonitrile phase;
  c) adding water to the cooled acetonitrile phase;

d) isolating the precipitated 2-chloro-4-(1-(tetrahydro-2H-pyran-2-yl)-1H-pyrazol-5-yl)benzonitrile of formula (III)

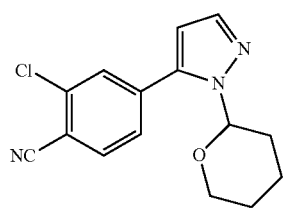

(III)

e) treating the compound of formula (III) with a catalytic amount of HCl in a methanol solvent;
f) adding a base to neutralize the mixture;
g) adding water to the mixture; and
h) isolating the precipitated compound of formula (V).

It was found that by changing the solvent in step a) to acetonitrile-water mixture and the catalyst to Pd(OAc)$_2$ and triphenylphosphine the amount of the expensive Pd catalyst can be substantially reduced. In particular, the amount of Pd(OAc)$_2$ per amount of 4-bromo-2-chlorobenzonitrile of formula (II) needed to carry out the Suzuki reaction effectively is as low as from about 0.5 to about 2 mol-%, preferably from about 0.6 to about 0.8 mol-%. Moreover, after completion of the Suzuki reaction the acetonitrile-water solvent forms two separate liquid phases and the isolation of the compound of formula (III) from the acetonitrile phase is easy without the need of any distillation steps.

The compounds of formula (I) and (II) are commercially available or they can be prepared according to methods known in the art.

For carrying out the Suzuki reaction, the mixture of acetonitrile, water, the base and 4-bromo-2-chlorobenzonitrile of formula (II) can be first refluxed under nitrogen atmosphere for about 15 to 60 min, for example about 30 min. The reaction is preferably carried out under nitrogen flow. Thus, air is removed, for example, by refluxing and replaced by nitrogen. In the acetonitrile-water solvent the ratio of acetonitrile to water is generally from about 25:75 to about 75:25, preferably from about 35:65 to about 65:35, more preferably from about 40:60 to about 60:40, for example 50:50, by volume. The base is suitably an inorganic base, preferably potassium carbonate.

The mixture is then suitably cooled to 60-70° C. and Pd(OAc)$_2$ and triphenylphosphine are added. The molar ratio of the Pd(OAc)$_2$ to triphenylphosphine to be used in the process is suitably about 1:3. The amount of Pd(OAc)$_2$ per amount of 4-bromo-2-chlorobenzonitrile of formula (II) is generally from about 0.5 to about 2 mol-%, preferably from about 0.6 to about 0.8 mol-%. Compound of formula (I) may be dissolved in acetonitrile and added slowly, for example during 0.5 h, to the mixture. The reaction mixture is then stirred for at a temperature from about 60 to about 75° C., preferably at 70±3° C., for a time period sufficient to complete the reaction, typically from about 1 to about 5 h, for example 2 h. Separate water and acetonitrile phases are formed and water phase can be discarded from the mixture suitably at the temperature of 65-70° C. A base, such as ammonia water (25%), can be added to the isolated acetonitrile phase at this stage in order to prevent possible detachment of the tetrahydropyranyl ring from the compound of formula (III). The compound of formula (III) can then be precipitated by cooling the mixture, for example to 20±5° C., and by adding gradually water to the cooled mixture. The amount of water to be added is suitably about 80-120%, for example about 100%, by volume of the acetonitrile solvent. The mixture can be stirred at 20±5° C. for a period to complete precipitation of the compound of formula (III), for example for about 6 to 24 h. The precipitated product can be isolated, for example by filtering, and washed with acetonitrile-water and dried for example at reduced pressure at about 50-60° C.

Moreover, it was found that the conversion of the compound of formula (III) to the compound of formula (V) can be carried out in a one-pot process without isolation of the compound of formula (IV). Distillation steps are not needed and the process can be carried out using only a catalytic amount of 30% aqueous HCl, which is much more practical than the use of ethanolic HCl. The isolation of the compound of formula (V) is easy and the process as a whole provides improved yield.

The conversion of the compound of formula (III) to the compound of formula (V) can be carried out by mixing the compound of formula (III), methanol and a small amount of 30% HCl (aqueous) suitably at lowered temperature, such as 0-15° C., for example 10±3° C. The amount of HCl can be from about 0.05 to about 0.1, for example 0.08, mole equivalents per one mole of the compound of formula (III). The mixture is stirred at the above temperature for a time period necessary for the tetrahydropyranyl ring detachment to occur, such as 0.5 to 5 h, for example 2 h. A base, for example ammonia water (25%), is then added to the mixture at the above temperature. Thereafter, water is added gradually, for example at 10-20° C., and the mixture is stirred, for example for a period of 6 to 24 h. The amount of water to be added is suitably about 30-50%, for example 35-40%, by volume of the methanol solvent. The compound of formula (V) can be precipitated by cooling the mixture, for example to about 0-5° C., and stirring at this temperature for a period of time sufficient to complete the precipitation, suitably from about 1 to about 8 h, for example from about 3 to about 5 h. The precipitated product can be isolated, for example by filtering, and washed with cold water:methanol mixture 3:1 and dried for example at reduced pressure at about 50-60° C.

The compound of formula (1A) can be prepared from the compound of formula (V), for example, using the methods described in WO 2011/051540 and WO 2012/143599. For example, according to one embodiment, the process for the preparation of the compound of formula (1A) comprises the steps of
i) reacting a compound of formula (V)

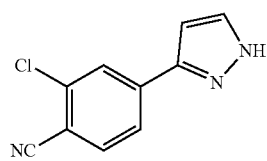

(V)

with a compound of formula (VI)

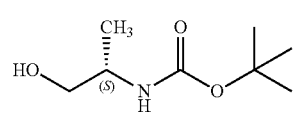

(VI)

to produce a compound of formula (VII);

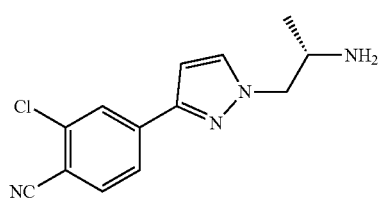

(VII)

j) reacting the compound of formula (VII) with a compound of formula (VIII)

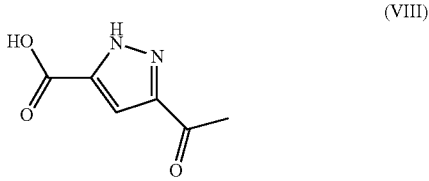

to produce a compound of formula (IX); and

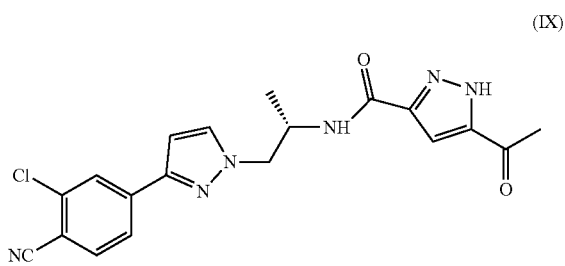 [SMILES: CC(=O)c1cc(C(=O)N[C@@H](C)Cn2ccc(-c3ccc(C#N)c(Cl)c3)n2)n[nH]1]

k) reducing the compound of formula (IX) to produce the compound of formula (1A).

The reaction of step i) can be carried out, for example, using the conditions of the Mitsunobu reaction, for example at room temperature in the presence of triphenylphosphine and DIAD (diisopropylazodicarboxylate) in a suitable solvent, for example THF or EtOAc, followed by Boc-deprotection by treatment with HCl and finally with a base such as NaOH.

The reaction step j) can be carried out at room temperature in the presence of suitable activating and coupling agent system such as a combination of DIPEA (N,N-diisopropylethylamine), EDCI (1-ethyl-3-(3-dimethylaminopropyl) carbodiimide) and anhydrous HOBt (1-hydroxy-benzotriazole) in a suitable solvent, for example DCM.

As an alternative to HOBt, HBTU (O-(benzotriazol-1-yl)-N,N,N',N'-tetramethyl-uroniumhexafluorophosphate) can be used. Alternatively, a combination of DIPEA and T3P (1-propanephosphonic acid cyclic anhydride) can be used as an activating and coupling agent system.

The reaction step k) can be carried out at room temperature by treating the compound of formula (IX) with a reduction agent, for example sodium borohydride, in a suitable solvent, for example ethanol, followed by treating the mixture with aqueous HCl.

The invention is further illustrated by the following non-limiting examples.

EXAMPLE 1

Preparation of 1-(tetrahydro-2H-pyran-2-yl)-5-(4,4,5,5-tetramethyl-1,3,2-dioxaborolan-2-yl)-1H-pyrazole of formula (I)

1-(Tetrahydro-2H-pyran-2-yl)-1H-pyrazole (5 kg), THF (7.0 l) and toluene (28 l) were mixed at room temperature (RT) under nitrogen atmosphere. The mixture was cooled to 0° C., n-BuLi (17.9 kg, 1.42 M in hexanes) was added dropwise at 0-5° C. over a period of 2-3 h and the mixture was stirred at 0-5° C. for 1 h. Triisopropyl borate (6.8 kg) was added dropwise at 0-5° C. over a period of 45 min. The mixture was brought to RT and stirred for 1-2 h. Pinacol (3.88 kg) was added portion wise to the mixture at RT over a period of 20-30 min followed by stirring for 45 min. The mixture was cooled to 0° C. and acetic acid (3.9 kg) was added dropwise over a period of 30 min at 0-5° C. The mixture was brought to RT and maintained for 12-14 h. The mixture was then cooled to 0° C. and water (20) was added dropwise at 0-5° C. over a period of 30 min. The mixture was brought to RT and stirred for 30 min. The aqueous layer was separated and extracted with toluene (20 l). The combined organic layer was washed with 10% NaHCO₃ solution (22 l) followed by water (20 l). The organic layer was concentrated under reduced pressure below 60° C. The obtained crude compound was then co-distilled with heptane (7 l). To the residue obtained heptane (5 l) was added and the mixture was stirred at 0-5° C. for 1-2 h. The solid was then filtered, washed with cold heptane (5 l) and dried at 25-30° C. for 2-3 h. Yield 6.2 kg (67.8%), HPLC purity 99.8.

EXAMPLE 2

Preparation of 2-chloro-4-(1-(tetrahydro-2H-pyran-2-yl)-1H-pyrazol-5-yl)benzonitrile (III)

Acetonitrile (50 ml), water (50 ml), potassium carbonate*H₂O (21.7 g, 2.07 eqv.) and 4-bromo-2-chlorobenzonitrile (II) (14.0 g, 1.00 eqv.) were charged. The mixture was refluxed under nitrogen atmosphere for about 0.5 h. The mixture was cooled to 60-70° C. under nitrogen protection. Palladium(II)acetate Pd(OAc)₂ (0.10 g, 0.007 eqv.) and triphenylphosphine (0.40 g, 0024 eqv.) were added under nitrogen protection. 1-(Tetrahydro-2H-pyran-2-yl)-5-(4,4,5,5-tetramethyl-1,3,2-dioxaborolan-2-yl)-1H-pyrazole (I) (21.0 g, 1.17 eqv.) was dissolved in acetonitrile (30 ml). Air was removed by vacuum and replaced by nitrogen. This solution was added to the reaction mixture in about 0.5 h at 70±3° C. The reaction mixture was stirred for 2 h at 70±3° C. The water phase was separated off and removed from the reaction mixture at 65-70° C. 2 ml of ammonia water (25%) was added to the reaction mixture which was then cooled to 20±5° C. Water (80 ml) was added gradually at 20±5° C. The mixture was stirred overnight at 20±5° C. The crystalline product was filtered and washed twice with acetonitrile:water 1:1 (20 ml). The product was dried under reduced pressure at 50-60° C. Yield 17.18 g (92.3%). HPLC-purity 99.8%.

EXAMPLE 3

Preparation of 2-chloro-4-(1H-pyrazol-3-yl)benzonitrile (V)

2-Chloro-4-(1-(tetrahydro-2H-pyran-2-yl)-1H-pyrazol-5-yl)benzonitrile (III) (10.0 g, 1.00 eqv.) and methanol (40 ml) were charged. 30% HCl (0.3 ml, 0.08 eqv.) was added at 10±3° C. The mixture was stirred for 2 h at 10±3° C. Ammonia water (25%) was added (3.0 ml, 1.1 eqv.) at 10±5° C. Water (15 ml) was added gradually at 10-20° C. The mixture was stirred overnight at 20±5° C. The mixture was then cooled to 0-5° C. and stirred for 4 h at 0-5° C. The crystalline product was filtered and washed with cold water:methanol mixture 3:1 (30 ml) and dried at 50-60° C. Yield 6.78 g (95.8%). HPLC-purity 99.7%.

EXAMPLE 4

Preparation of (S)-4-(1-(2-aminopropyl)-1H-pyrazol-3-yl)-2-chlorobenzonitrile (VII)

15 g (73.7 mmol) of 2-Chloro-4-(1H-pyrazol-3-yl)benzonitrile (V), 26.5 g (151 mmol) of (S)-tert-butyl-1-hydroxypropan-2-ylcarbamate (VI), triphenylphosphine (39.6 g, 151 mmol) and 84 ml of EtOAc were placed into the reaction vessel under nitrogen atmosphere. The mixture was cooled to 10±5° C. DIAD (29.7 ml, 151 mmol) was added evenly during 4 h under stirring while keeping the temperature at 10±10° C. The mixture was warmed to 20±5° C. and stirred overnight. Concentrated HCl (31.1 ml, 295 mmol) was added dropwise during 10-30 min under stirring while keeping the temperature at 30±5° C. The mixture was stirred at 45±5° C. until the reaction was completed. Water (82.5 ml) was added and the temperature was adjusted to 35±5° C. DCM (105 ml) was then added and the mixture was stirred vigorously for at least for 1 min and the layers were let to separate for 10 min. The organic layer was isolated and was washed with 60 ml of warm water. Water phases were combined and washed with 75 ml of DCM. Thereafter 75 ml of DCM and 19.3 ml (125 mmol) of 25% ammonium solution (NH$_4$OH) was added to the water phase. pH was set to over 9 by addition of 50% NaOH and the mixture was stirred at 40±5° C. until the reaction was completed. pH was set to over 9 by addition of 50% NaOH. The solution was filtered through the celite at 35° C., layers were separated and the organic phase was isolated. DCM was distilled out at normal pressure until 25 ml of the solution was left. 2-Propanol (4.65 ml) was added and the temperature was adjusted to about 50° C. Thereafter 90 ml of N-heptane was added during 1 h. The solution was seeded when about 22 ml of N-heptane had been added. The mixture was cooled to 0±5° C. during 6 h and then stirred overnight. The precipitated product was isolated by filtering, washed with N-heptane (30 ml) and dried under vacuum at 50° C. Yield 81.8%.

EXAMPLE 5

Preparation of 3-acetyl-1H-pyrazole-5-carboxylic acid (VIII)

3-Acetyl-1H-pyrazole-5-carboxylate (5 g, 29.7 mmol), water (30 ml) and sodium hydroxide 48% (2.83 ml, 52.0 mmol) were carefully added into the reaction vessel. The mixture was warmed to 60-65° C. and stirred until the reaction was completed. The mixture was then cooled to 50° C. 30% HCl (2.83 ml, 26.8 mmol) was added at 50° C. during 1 h and the mixture was seeded at the end of the HCl addition. The mixture was stirred for 2 h. Further 30% HCl (2.451 ml, 23.19 mmol) was added at 50° C. during 3 h followed by stirring at 50° C. for 30 min. The precipitated product was isolated by filtering, washed with water (5 ml) and then with methanol (2.5 ml) and dried under vacuum at 60° C. Yield 92.8%.

EXAMPLE 6

Preparation of (S)-5-acetyl-N-(1-(3-(3-chloro-4-cyanophenyl)-1H-pyrazol-1-yl)propan-2-yl)-1H-pyrazole-3-carboxamide (IX)

6.80 g (44.1 mmol) of 3-acetyl-1H-pyrazole-5-carboxylic acid (VIII), DCM (76 ml), 10.33 g (38.3 mmol) of(S)-4-(1-(2-aminopropyl)-1H-pyrazol-3-yl)-2-chlorobenzonitrile (VII) and DIPEA (18.04 ml, 104 mmol) were placed in to the reaction flask under nitrogen atmosphere at about 20° C. The mixture was cooled to 5° C. Thereafter 28.2 ml (49.9 mmol) of T3P (1-propanephosphonic acid cyclic anhydride) in EtOAc (50%) was added during 2 h under vigorous stirring at about 10° C. The mixture was stirred at 10±3° C. overnight. Thereafter ethanol (30 ml) was added to the mixture. About 70 ml of DCM was then distilled off at about 60° C. and the mixture was seeded at about 60° C. followed by stirring for 30 min at this temperature. A mixture of water (40 ml), 0.75 ml of 30% HCl in water and ethanol (10 ml) was then added during about 2 h followed by stirring at 60±5° C. for about 2 h. The mixture was cooled to 5-10° C. during 4 h followed by stirring at this temperature overnight. The precipitated product was isolated by filtering, washed with 2×30 ml of water and 1×20 ml of ethanol, and dried under vacuum at 60° C. overnight. Yield 87.5%.

EXAMPLE 7

Preparation of N—((S)-1-(3-(3-chloro-4-cyanophenyl)-1H-pyrazol-1-yl)-propan-2-yl)-5-(1-hydroxy-ethyl)-1H-pyrazole-3-carboxamide (IA)

100 mg (0.25 mmol) of (S)-5-acetyl-N-(1-(3-(3-chloro-4-cyanophenyl)-1H-pyrazol-1-yl)propan-2-yl)-1H-pyrazole-3-carboxamide (IX) and 5 ml of EtOH were put to reaction flask and 19 mg (0.5 mmol) of sodium borohydride was added slowly as EtOH suspension. The reaction was stirred overnight to completion. 0.5 ml of water and 1 ml of 0.5 M HCl were added dropwise. The solution was evaporated to dryness and 20 ml of DCM was added. The mixture was washed with 10 ml of 1 M NaHCO$_3$ and 10 ml of water followed with drying over Na$_2$SO$_4$. After filtration and evaporation 76 mg of the product was obtained. Yield 76%.

The invention claimed is:
1. A method for preparing 2-chloro-4-(1H-pyrazol-3-yl) benzonitrile of formula (V)

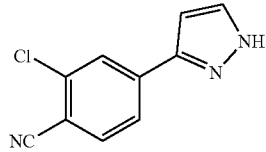

(V)

comprising the steps of
a) reacting 1-(tetrahydro-2H-pyran-2-yl)-5-(4,4,5,5-tetramethyl-1,3,2-dioxaborolan-2-yl)-1H-pyrazole of formula (I)

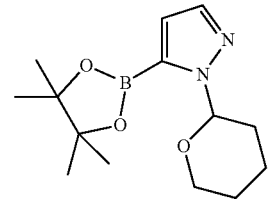

(I)

with 4-bromo-2-chlorobenzonitrile of formula (II)

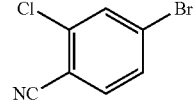

(II)

at an elevated temperature in the presence of Pd(OAc)$_2$, triphenylphosphine and a base in an acetonitrile-water solvent to form 2-chloro-4-(1-(tetrahydro-2H-pyran-2-yl)-1H-pyrazol-5-yl)benzonitrile of formula (III)

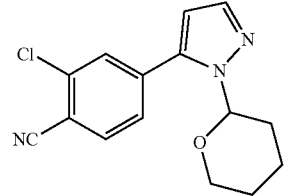

(III)

b) treating the compound of formula (III) with a catalytic amount of HCl in a methanol solvent;
c) adding a base to neutralize the mixture; and
d) isolating the compound of formula (V).

2. The method according to claim 1, wherein step a) further comprises
   i) isolating the acetonitrile phase;
   ii) cooling the acetonitrile phase;
   iii) adding water to the cooled acetonitrile phase; and
   iv) precipitating 2-chloro-4-(1-(tetrahydro-2H-pyran-2-yl)-1H-pyrazol-5-yl)-benzonitrile of formula (III)

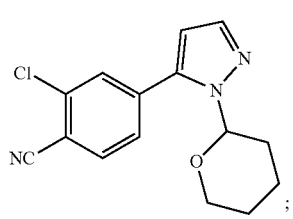

and
   wherein step c) further comprises
   i) adding water to the mixture; and
   ii) precipitating the compound of formula (V).

3. The method according to claim 1, wherein the amount of Pd(OAc)$_2$ used per amount of compound of formula (II) in step a) is from about 0.5 to about 2 mol-%.

4. The method according to claim 3, wherein the amount of Pd(OAc)$_2$ used per amount of compound of formula (II) in step a) is from about 0.6 to about 0.8 mol-%.

5. The method according to claim 1, wherein the molar ratio of the Pd(OAc)$_2$ to triphenylphosphine is 1:3.

6. The method according to claim 1, wherein the base is potassium carbonate.

7. The method according to claim 1, wherein the reaction temperature at step a) is from about 60° C. to about 75° C.

8. The method according to claim 7, wherein the reaction temperature at step a) is from 67° C. to 73° C.

9. The method according to claim 1, wherein step a) is carried out under nitrogen flow.

10. The method according to claim 2, wherein step a) further comprises adding a base to the isolated acetonitrile phase after step ai) and before step aii).

11. The method according to claim 10, wherein the base is ammonia water.

12. The method according to claim 2, wherein the temperature of the mixture after step aiii) is 10° C. to 40° C.

13. The method according to claim 12, wherein the temperature of the mixture after step aiii) is 20° C. to 25° C.

14. The method according to claim 1, wherein the reaction time at step a) is 1 hour to 8 hours.

15. The method according to claim 14, wherein the reaction time at step a) is 2 hours to 4 hours.

16. The method according to claim 1, wherein the amount of HCl used per amount of compound of formula (III) in step b) is from about 0.05 to about 0.2 molar equivalents.

17. The method according to claim 16, wherein the amount of HCl used per amount of compound of formula (III) in step b) is from about 0.07 to about 0.10 molar equivalents.

18. The method according to claim 1, wherein the reaction temperature at step b) is 0° C. to 20° C.

19. The method according to claim 18, wherein the reaction temperature at step b) is 5° C. to 15° C.

20. The method according to claim 1, wherein the reaction time at step b) is 1 hour to 8 hours.

21. The method according to claim 20, wherein the reaction time at step b) is 2 hours to 4 hours.

22. The method according to claim 1, wherein the base used at step c) is ammonia water.

23. The method according to claim 2, wherein the temperature of the mixture after step ci) is 10° C. to 20° C.

24. The method according to claim 2, wherein the isolation at step d) is carried out at 0° C. to 5° C.

25. A method for preparing 2-chloro-4-(1H-pyrazol-3-yl)benzonitrile of formula (V)

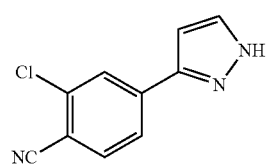

comprising the steps of
   a) treating 2-chloro-4-(1-(tetrahydro-2H-pyran-2-yl)-1H-pyrazol-5-yl)benzonitrile of formula (III)

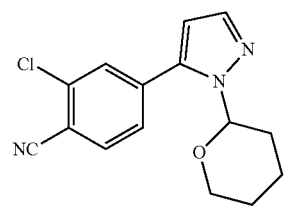

with a catalytic amount of HCl in a methanol solvent;
   b) adding a base to neutralize the mixture;
   c) precipitating the compound of formula (V); and
   c) isolating the precipitated compound of formula (V).

26. The method according to claim 25, wherein step b) further comprises adding water to the mixture after step b) and before step c).

27. A method for preparing 2-chloro-4-(1-(tetrahydro-2H-pyran-2-yl)-1H-pyrazol-5-yl)benzonitrile of formula (III)

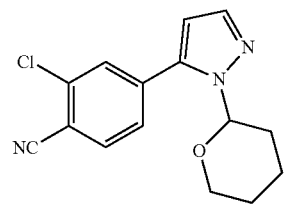

comprising the steps of
   a) reacting 1-(tetrahydro-2H-pyran-2-yl)-5-(4,4, 5-tetra e hyl-1,3,2- dioxaborolan-2-0-1H-pyrazole of formula (I)

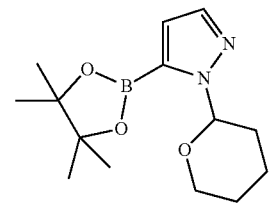

with 4-bromo-2-chlorobenzonitrile of formula (II)

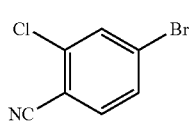
(II)

at an elevated temperature in the presence of Pd(OAc)$_2$, triphenylphosphine and a base in an acetonitrile-water solvent.

28. The method according to claim 27, further comprising the steps of
   b) isolating the acetonitrile phase;
   c) cooling the acetonitrile phase;
   d) adding water to the cooled acetonitrile phase;
   e) precipitating the compound of formula (III); and
   e) isolating the precipitated compound of formula (III).

29. A method for preparing the compound of formula (1A)

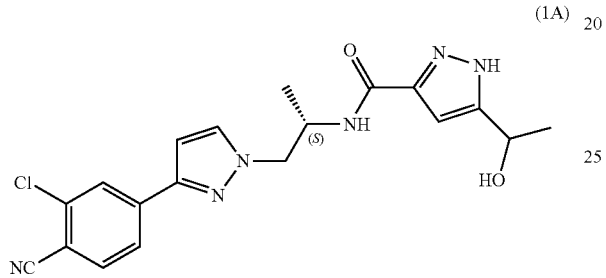
(1A)

comprising the steps of
   a) reacting a compound of formula (V)

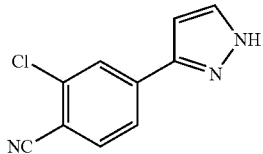
(V)

with a compound of formula (VI)

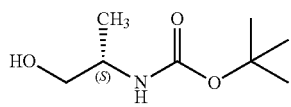
(VI)

to produce a compound of formula (VII)

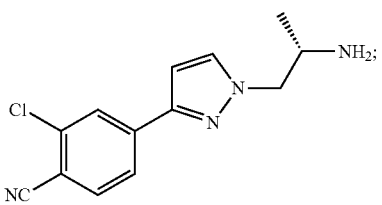
(VII)

and
   b) reacting the compound of formula (VII) with a compound of formula (VIII)

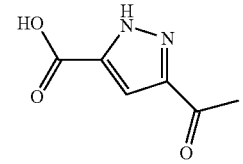
(VIII)

to produce a compound of formula (IX)

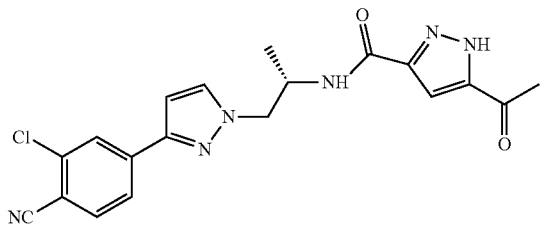
(IX)

and
   c) reducing the compound of formula (IX) to produce the compound of formula (1A);
   wherein the compound of formula (V) is prepared according to claim 1.

* * * * *

UNITED STATES PATENT AND TRADEMARK OFFICE
CERTIFICATE OF CORRECTION

PATENT NO. : 10,189,789 B2
APPLICATION NO. : 15/564878
DATED : January 29, 2019
INVENTOR(S) : Ilpo Laitinen et al.

Page 1 of 1

It is certified that error appears in the above-identified patent and that said Letters Patent is hereby corrected as shown below:

In the Claims

Claim 27, Column 16, Line 52:
"1-(tetrahydro-2H-pyran-2-yl)-5-(4,4, 5-tetra e hyl-1,3,2- dioxaborolan-2-0-1H-pyrazole"
Should read as:
--1-(tetrahydro-2H-pyran-2-yl)-5-(4,4,5,5-tetramethyl-1,3,2-dioxaborolan-2-0-1H-pyrazole--.

Claim 28, Column 17, Line 17:
"e) isolating the precipitated compound of formula (III)."
Should read as:
--f) isolating the precipitated compound of formula (III).--.

Signed and Sealed this
Second Day of July, 2019

Andrei Iancu
*Director of the United States Patent and Trademark Office*